United States Patent [19]

Hunt

[11] Patent Number: 4,977,893
[45] Date of Patent: Dec. 18, 1990

[54] SURGICAL HIP WRAP

[75] Inventor: James R. Hunt, Carencro, La.

[73] Assignee: Surgical Specialties, Inc., Lafayette, La.

[21] Appl. No.: 380,605

[22] Filed: Jul. 17, 1989

[51] Int. Cl.⁵ ............................................. A61F 13/00
[52] U.S. Cl. .................................. 128/157; 128/846; 128/165; 128/96.1
[58] Field of Search ................... 128/94, 95.1, 96.1, 128/100.1, 101.1, 112.1, 846, 891, 876, 160, 165, 152

[56] References Cited

U.S. PATENT DOCUMENTS

| | | | |
|---|---|---|---|
| 976,550 | 7/1910 | Coddington. | |
| 2,596,275 | 5/1952 | Muller | 128/171 |
| 2,926,665 | 8/1960 | Seese | 128/155 |
| 3,125,093 | 11/1964 | Hutchins | 128/283 |
| 3,490,449 | 9/1970 | Ewerwahn | 128/157 |
| 3,526,221 | 9/1970 | Garber | 128/95.1 |
| 3,529,601 | 1/1971 | Kirkland | 128/293 |
| 3,754,549 | 8/1973 | Nelkin | 128/100.1 |
| 3,933,150 | 4/1976 | Kaplan et al. | 128/24 R |
| 4,644,946 | 12/1987 | Cremona-Bonato | 128/165 |
| 4,802,667 | 2/1989 | Altner | 128/78 |
| 4,829,994 | 5/1989 | Kurth | 128/96.1 |

Primary Examiner—Robert A. Hafer
Assistant Examiner—Kerry Owens
Attorney, Agent, or Firm—George A. Bode; Michael L. Hoelter

[57] ABSTRACT

A surgical hip wrap comprising an elongated fabric strip that is wrapped around a hip of a user to cover and/or protect it. The fabric strip is held in place by securing one end region around the waist of the user and by securing the opposite end region around the adjacent upper thigh region of the user. These end regions are secured to the fabric strips such as by a hook and loop closure system or adhesives or the like. The non-linear opposite end regions are offset one from the other, but they extend along generally parallel lines.

7 Claims, 3 Drawing Sheets

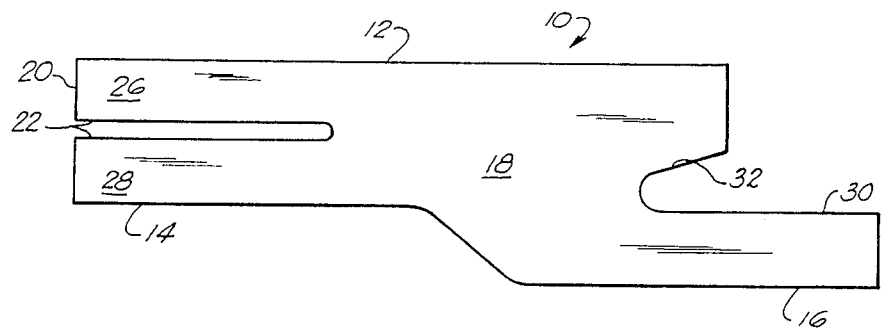
FIG. 5
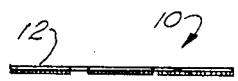
FIG. 4
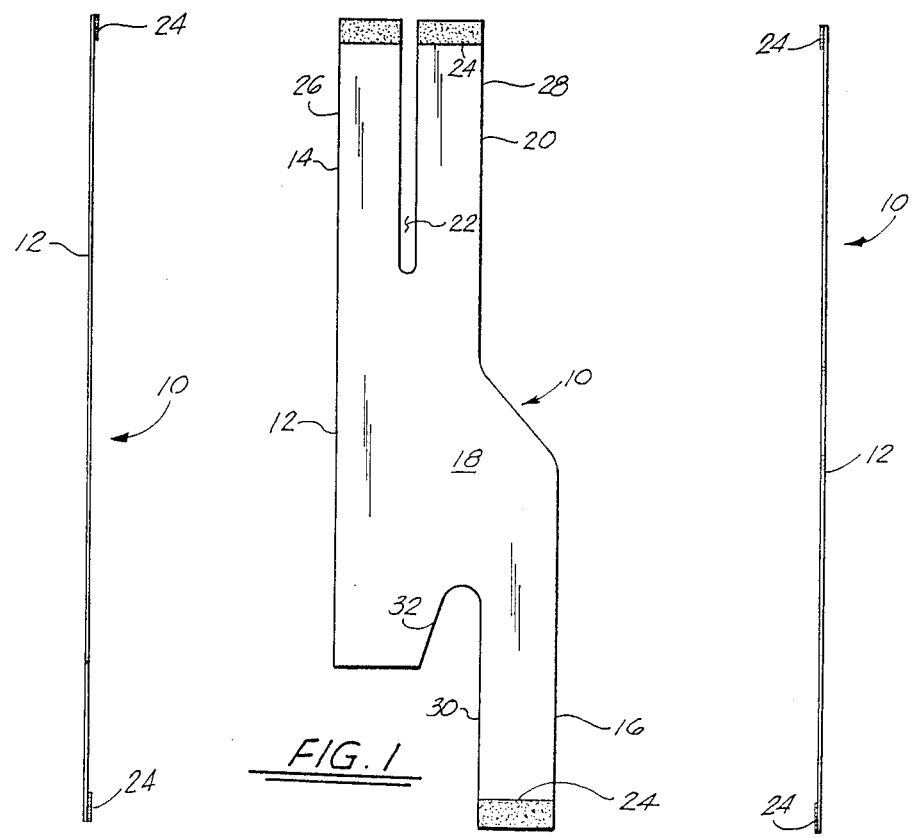
FIG. 1
FIG. 2
FIG. 3
FIG. 6

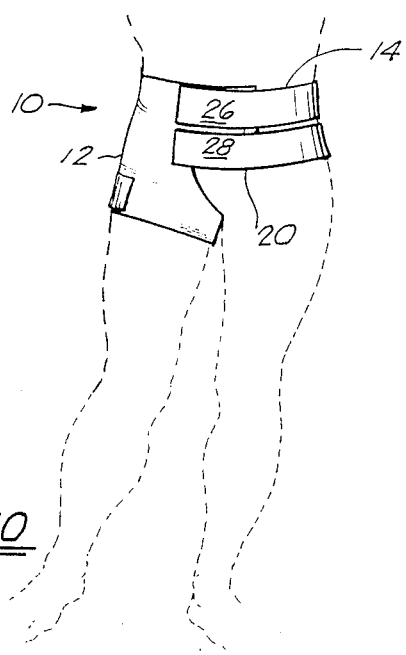
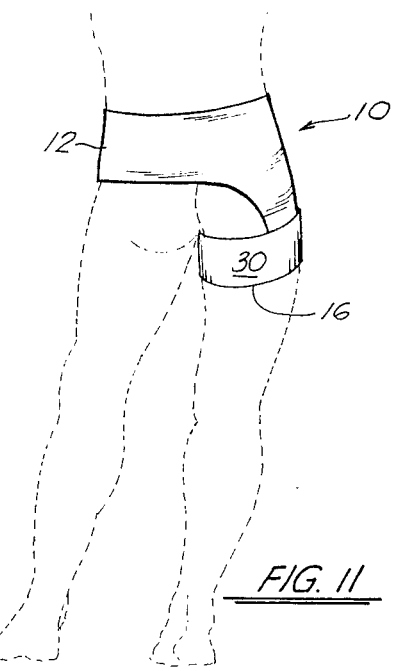
FIG. 10
FIG. 11
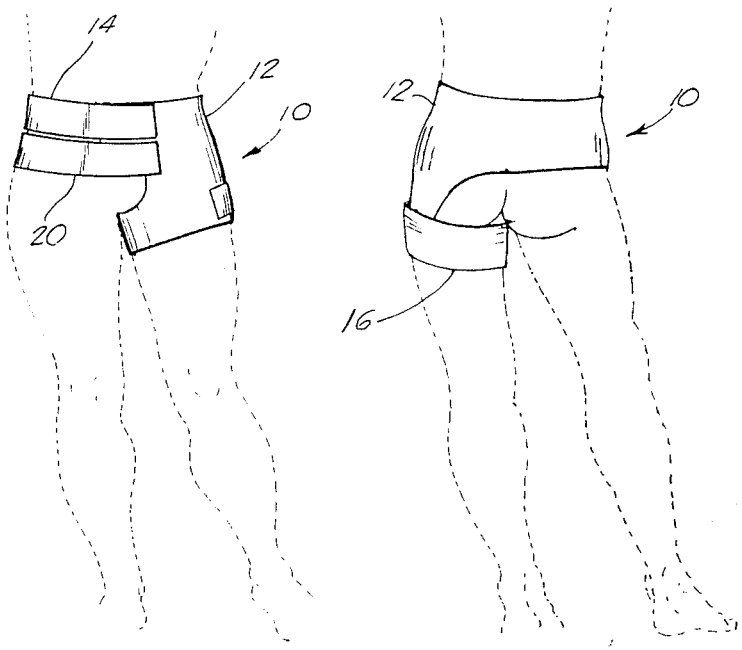
FIG. 12
FIG. 13

SURGICAL HIP WRAP

BACKGROUND OF THE INVENTION

1. Field of the Invention

The present invention relates to medical bandages and more particularly, to an adjustable hip wrap for covering surgical dressings, wounds, and the like.

2. General Background

The medical arts include a vast number of coverings for wounds and the like. Some are mere strips of fabric while others more elaborately incorporate buckles, zippers, straps, etc.

Typical examples of the simpler type of strip bandages are U.S. Pat. No. 2,596,275 issued to C. A. Muller; U.S. Pat. No. 3,490,449 issued to W. J. Ewerwahn; U.S. Pat. No. 3,529,601 issued to J. W. Kirkland; and, U.S. Pat. No. 3,125,093 issued to F. D. Hutchins. Each of these are wrapped around a body part, usually the torso, with the tightness of the wrap holding the bandage in place. Unfortunately, the bandage follows the laws of nature and moves in the direction of least resistance meaning that it may creep or move along the body part. Also, the bandage may rotate or slide around or with respect to the body part if not properly restrained.

To overcome this, such devices as adhesives, belts, straps, buckles, hook and loop closure systems, etc. have been applied to the bandage. Additionally, the bandages or coverings were designed to conform to a specific body part or need. Examples of the latter include U.S. Pat. No. 976,550 issued to R. V. Coddington; U.S. Pat. No. 2,926,665 issued to G. E. Seese; U.S. Pat. No. 3,933,150 issued to David Clark Company Incorporated on the application of B. H. Kaplan et al.; and, U.S. Pat. No. 4,644,946 issued to G. Cremona-Bonato. To make these specific body part bandages or coverings more adaptable to a variety of differently shaped bodies, straps or other adjustable means were incorporated into their design. Unfortunately, however, they do not enjoy the same degree of flexibility and ease of application to the body part as the simple strip bandages have. Another disadvantage of these specific type bandages is that they sometimes are too specific, i.e. the same bandage may not always be used on both the right and left (or front and back) sides of the body. To accomplish this, two separate bandages would be required.

It is thus an object of this invention to provide a surgical wrap or dressing that is specific to a certain body part while also retaining the ease of application enjoyed by simple strip bandages. Another object of this invention is to provide a surgical wrap or dressing that is specific to the hip region of a body while being equally applicable to either hip of the body. A further object of this invention is to provide a single surgical hip wrap that can accommodate the hips of very large persons all the way down to the hips of very small persons. Yet another object of this invention is to provide a hip wrap that is easily removed and/or adjusted so that the injury may be quickly accessed or pressure on the injury promptly relieved. These and other objects of this invention will become obvious upon further investigation.

SUMMARY OF THE PRESENT INVENTION

The preferred embodiment of the apparatus of the present invention solves the aforementioned problems in a straight forward and simple manner. What is provided is a surgical hip wrap for protecting the hip area of a user comprising an elongated strip of fabric that wraps around the waist and an adjacent upper thigh region of a user before being attached back onto itself. This hip wrap includes opposite, offset extensions projecting away from the fabric strip each of which include separate securing means for securing that extension to the hip wrap after being wrapped around its respective body part. The width of the intermediate region of the hip wrap is wider than either such extension and this hip wrap includes a notch adjacent the thigh extension that is configured for placement around the crotch region of the user, thereby permitting access to this area without requiring the removal of the hip wrap.

BRIEF DESCRIPTION OF THE DRAWINGS

For a further understanding of the nature and objects of the present invention, reference should be had to the following description taken in conjunction with the accompanying drawing in which like parts are given like reference numerals and, wherein:

FIG. 1 is a rear planar view of the preferred embodiment of the apparatus of the present invention;

FIG. 2 is a top side view of the embodiment of FIG. 1;

FIG. 3 is a bottom side view of the embodiment of FIG. 1;

FIG. 4 is an end view of the embodiment of FIG. 1;

FIG. 5 is a front planar view of the embodiment of FIG. 1;

FIG. 6 is an end view of the embodiment of FIG. 1, this end view being an end view opposite that shown in FIG. 4;

FIG. 10 is a front pictorial view of the embodiment of FIG. 1 wrapped around a user's right hip;

FIG. 11 is a rear pictorial view of the embodiment of FIG. 1 wrapped around a user's right hip;

FIG. 12 is a front pictorial view of the embodiment of FIG. 1 wrapped around a user's left hip; and, FIG. 13 is a rear pictorial view of the embodiment of FIG. 1 wrapped around a user's left hip.

DETAILED DESCRIPTION OF THE PREFERRED EMBODIMENT

Figure 7:
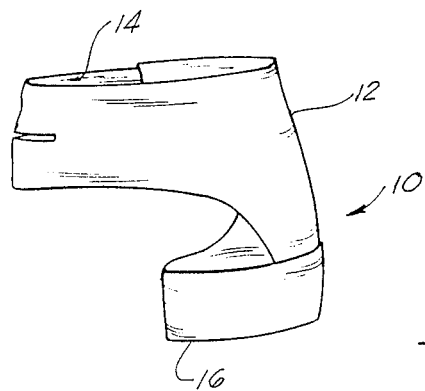
FIG. 7 is a front pictorial view of the embodiment of FIG. 1.

Referring now to the drawings, and in particular FIGS. 1-5, there is shown hip wrap 10 comprising a planar fabric strip 12 having a configuration essentially as disclosed. All or a portion of fabric strip 12 may be constructed of an absorbent material such as cotton or linen, or it may be constructed of a nonabsorbent material such as nylon, rayon, polyester, etc. Preferably, fabric strip 12 is constructed of a material that has some 'stretch' or 'give' to it to increase its comfort while being worn. Some conditions, however, may dictate otherwise.

Figure 8:
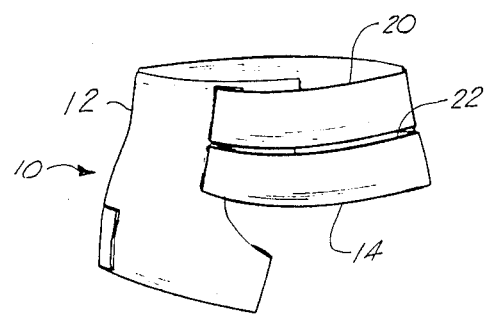
FIG. 8 is a rear pictorial view of the embodiment of FIG. 1.
Figure 9:
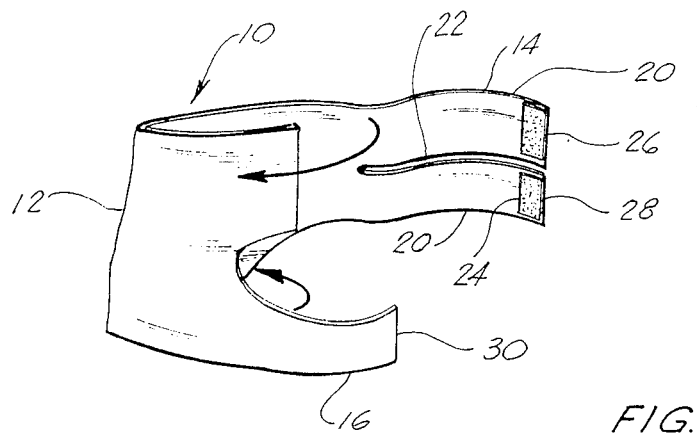
FIG. 9 is a rear pictorial view of the embodiment of FIG. 1 illustrating its operation and method of attachment to a user.

As shown in greater detail in FIGS. 1 and 5, hip wrap 10 is configured having waist end region 14, thigh end region 16, and intermediate region 18. In the preferred embodiment, waist end region 14 comprises two elongated extensions 20, but it should be noted that more or less than two such extensions may be possible. These waist extensions 20 are co-planar and extend parallel to each other, there being a small gap 22 between them. At the extreme end of each extension 20 are means 24 for securing that extension around the waist of a user and back onto hip wrap 10. These means 24 may consist of half a hook and loop closure system or it may consist of adhesive or other chemical or mechanical fastening means that attach to hip wrap 10. No matter its method of attachment, each waist extension 20 is independently wrapped around the waist of a user and secured in place (FIGS. 7, 8 and 9). By incorporating two independent waist extensions, they may each be secured without regard to the position of the other. In this fashion, top extension 26 may actually wrap around the waist of the user while bottom extension 28 may be secured around the abdomen or one hip of the user.

Similar to waist end region 14, thigh end region 16 incorporates thigh extension 30. While all these extensions 20 and 30 are co-planar, they are not colinear, but they do extend along parallel lines, or at least in generally parallel directions. Thigh extension 30 also has means 24 at its end for securing thigh extension 30 around the upper thigh region of a user.

Adjacent thigh extension 30, is notch 32 which projects partially into intermediate region 18. Notch 32 is sized to eliminate any pressure on the crotch region of a user when hip wrap 10 is used. Obviously, then, notch 32 is placed around the user's crotch whenever waist extension 20 and thigh extension 30 are being secured around their respective portions of the user.

Intermediate region 18 has a width equal to at least the cumulative width of extensions 20 and 30. Neither extensions 20 nor 30 are secured to intermediate region 18 in a symmetrical fashion, instead, they are both offset toward opposite sides of intermediate region 18. It is this intermediate region 18 that is placed around the hip region of the user that is to be covered by hip wrap 10. Extension 20 and 30 are designed to simply retain intermediate region 18 in place against the user.

As shown in better detail in FIGS. 7-13, hip wrap 10 incorporates two separate extensions for securing hip wrap 10 around a user. During attachment, a user would position intermediate region 18 against the hip region to be covered with notch 32 positioned adjacent the user's crotch region. Then, waist extension 20 and thigh extension 30 are secured in place around, respectively, the waist and one thigh of a user as indicated. Means 24 would secured extensions 20 and 30 to different portions of hip wrap 10.

Preferably, means 24 for securing hip wrap 10 around the user would be located on both sides of hip wrap 10. This way, hip wrap 10 could be used to cover and protect either the right or the left hip of the user as shown in FIGS. 10-13. Also, as shown in these drawings, the buttocks and crotch area of the user are not covered so as to increase the comfort of the user and to eliminate the need to remove hip wrap 10 under certain conditions.

It should also be reiterated that intermediate region 18 may be constructed of cotton or other absorbent, sterile or breathable dressing while waist end region 14 and thigh end region 16 may be constructed of another material that is better suited for securing hip wrap 10 in place.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. An elongated fabric strip configured to independently wrap around the waist and one upper thigh of a user, thereby covering and protecting a hip region, said one upper thigh of said user being the thigh adjacent the hip to be covered and protected by said fabric strip, said strip comprising:
   (a) first securing means for securing a first end region of said fabric strip around the waist of said user, said first securing means comprising two or more elongated planar extensions, separately by a gap, each configured to wrap around the waist region of said user;
   (b) second securing means for securing a second end region of said fabric strip around said one upper thigh of said user, thereby positioning an intermediate region of said fabric strip against a hip region of said user, said second securing means comprising an elongated extension configured to wrap around said upper thigh of said user;
   (c) said elongated extensions of said first and second securing means projecting outwardly in opposite directions away from said intermediate region, said intermediate region being wider than either of said extension, said extensions of said first and second securing means being not co-linear and offset one from the other, but extending along generally parallel lines; and
   (d) a notch adjacent said second securing means and projecting concavely into said intermediate region, said notch being configured to accommodate the crotch region of a user when said fabric strip is used.

2. The apparatus of claim 1, wherein said first and second securing means comprise part of a hook and loop closure system.

3. The apparatus of claim 1, wherein said first and second securing means comprises an adhesive for bonding to said fabric strip.

4. A hip wrap comprising:
   (a) a fabric strip having co-planar waist and thigh extensions projecting away from said strip in opposite directions, said waist and thigh extensions being not co-linear and offset from each other, but extending along parallel lines, said waist extension comprising a plurality of members that are each independently wrapped around the waist of a user;
   (b) holding means attached to the outermost regions of each waist and thigh extension for securing said extensions around, respectively, the waist and one thigh of a user, said holding means positioned on a first side of said fabric strip and when wrapped around a user, are secured to a second, opposite side of said fabric strip; and
   (c) a notch adjacent said thigh extension in said fabric strip, said notch configured to accommodate the crotch region of said user when said fabric strip is used.

5. The apparatus of claim 4, further comprising an intermediate region intermediate said waist and thigh extensions, said intermediate region being wider than the width of either said extension.

6. The apparatus of claim 5, wherein said holding means comprise part of a hook and loop closure system.

7. The apparatus of claim 5, wherein said holding means comprise an adhesive for bonding to said hip wrap.

* * * * *